United States Patent
Kim et al.

(10) Patent No.: US 10,238,624 B2
(45) Date of Patent: Mar. 26, 2019

(54) COMPOSITION FOR ACTIVATING LONGEVITY GENES, CONTAINING KOJIC ACID DERIVATIVE AS ACTIVE INGREDIENT

(71) Applicant: AMOREPACIFIC CORPORATION, Seoul (KR)

(72) Inventors: Hyun Jung Kim, Yongin-si (KR); Ji Hyun Kim, Yongin-si (KR); Jue Won Kim, Yongin-si (KR); Ho Sik Rho, Yongin-si (KR); Hyun Seo Kang, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/563,119

(22) PCT Filed: Mar. 28, 2016

(86) PCT No.: PCT/KR2016/003116
§ 371 (c)(1),
(2) Date: Sep. 29, 2017

(87) PCT Pub. No.: WO2016/159604
PCT Pub. Date: Oct. 6, 2016

(65) Prior Publication Data
US 2018/0078522 A1 Mar. 22, 2018

(30) Foreign Application Priority Data

Mar. 31, 2015 (KR) .................. 10-2015-0045129
Mar. 31, 2015 (KR) .................. 10-2015-0045227

(51) Int. Cl.
*A61K 31/351* (2006.01)
*A61K 31/35* (2006.01)
*A61K 31/36* (2006.01)
*A61K 8/49* (2006.01)
*A61Q 19/00* (2006.01)

(52) U.S. Cl.
CPC .............. *A61K 31/351* (2013.01); *A61K 8/49* (2013.01); *A61K 8/498* (2013.01); *A61K 31/35* (2013.01); *A61K 31/36* (2013.01); *A61Q 19/00* (2013.01); *A61Q 19/007* (2013.01)

(58) Field of Classification Search
CPC .... A61K 8/498; A61K 31/351; A61K 31/357; A61K 31/36; A61K 8/49; A61Q 19/00; A61Q 19/007
See application file for complete search history.

(56) References Cited

U.S. PATENT DOCUMENTS 6,916,844 B2   7/2005 Roh et al.

FOREIGN PATENT DOCUMENTS

| KR | 10-2004-0000638 A | 1/2004 |
| KR | 10-2004-0025954 A | 3/2004 |
| KR | 10-2013-0026626 A | 3/2013 |

OTHER PUBLICATIONS

Sanchez et. al., Journal of Medicinal Chemistry, 1992, American Chemical Society, vol. 35(10), pp. 1764-1773 (Year: 1992).*
Friden-Saxin et. al., Journal of Medicinal Chemistry, 2012, American Chemical Society, vol. 55, pp. 7104-7113 (Year: 2012).*
Bhatia et. al., Nature Biotechnology, 2012, Nature Publishing Group, vol. 30(7), pp. 604-610 (Year: 2012).*
Cao et. al., Nature Reviews Cancer, 2011, Nature Publishing Group, vol. 11, pp. 749-754 (Year: 2011).*
Hsu et. al., The International Journal of Biochemistry & Cell Biology, 2014, Elsevier, vol. 53, pp. 361-371 (Year: 2014).*
Marchal et. al., Annals of the New York Academy of Sciences, 2013, New York Academy of Sciences, vol. 1290, pp. 67-73 (Year: 2013).*
International Search Report for PCT/KR2016/003116 (dated Oct. 25, 2016).
International Preliminary Report on Patentability for PCT/KR2016/003116 (dated Oct. 3, 2017).
Written Opinion for PCT/KR2016/003116 (dated Oct. 25, 2016).
Kim et al., "The effects of a novel synthetic retinoid, seletinoid G, on the expression of extracellular matrix proteins in aged human skin in vivo," Clinica Chimica Acta, 36:161-169 (2005).
Rho et al., "Kojyl cinnamate ester derivatives promote adiponectin production during adipogenesis in human adipose tissue-derived mesenchymal stem cells," Bioorganic & Medicinal Chemistry Letters, 24:2141-2145 (2014).
Kang, "Photoaging and Tretinoin," Dermatologic Clinics, Dermatologic Therapy, 16(2):357-364 (1998).

* cited by examiner

*Primary Examiner* — Sarah Pihonak
(74) *Attorney, Agent, or Firm* — Merchant & Gould P.C.

(57) ABSTRACT

Disclosed is a composition for activating longevity genes, particularly, a Sirt-1, Klotho, XPD, ERCC8 or FoxO3a gene, containing a kojic acid derivative as an active ingredient. The composition activates longevity genes, thereby having anticancer, lifetime extension, skin moisturization or skin barrier strengthening effects.

6 Claims, 3 Drawing Sheets

[Fig. 1]
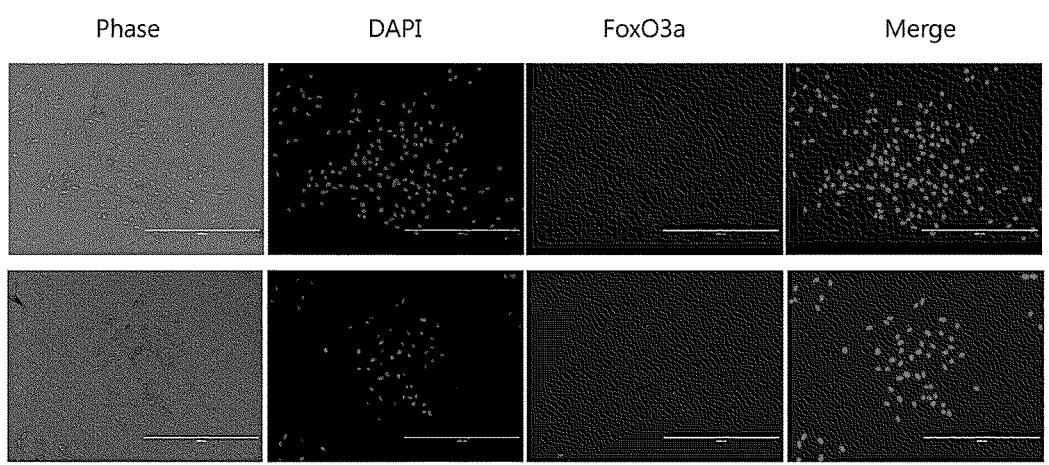
[Fig. 2]
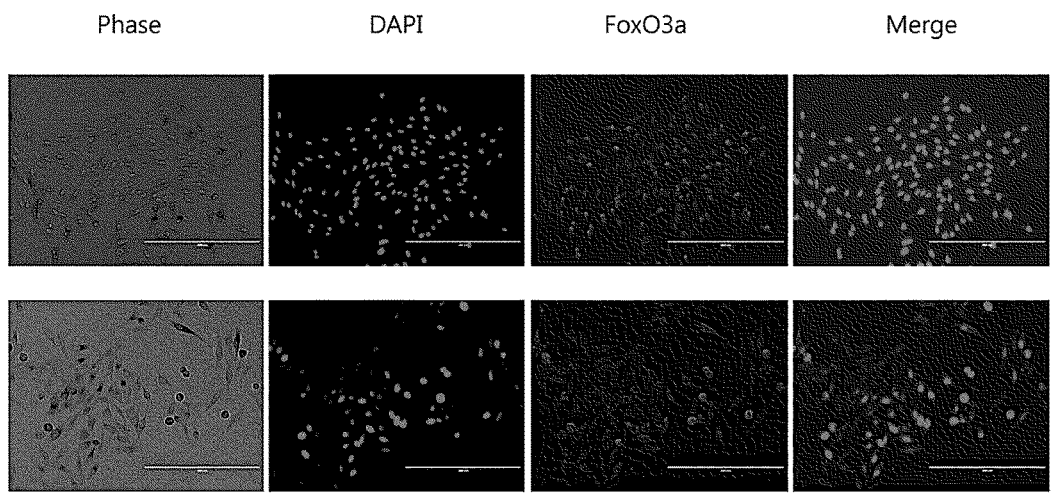

[Fig. 3]
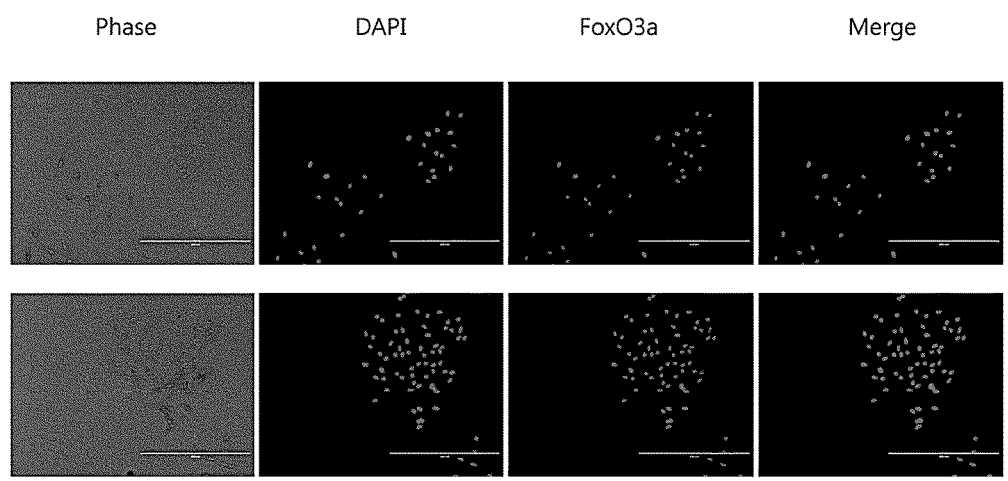
[Fig. 4]
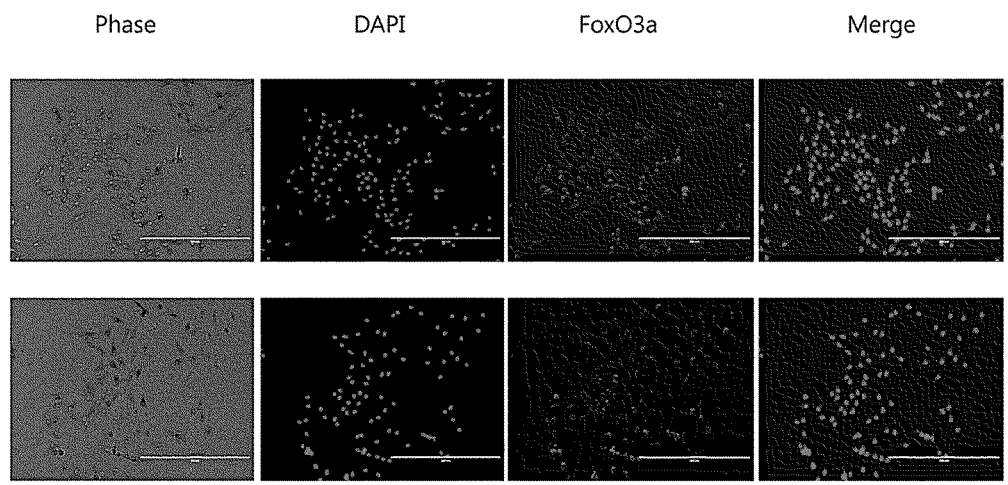

[Fig. 5]
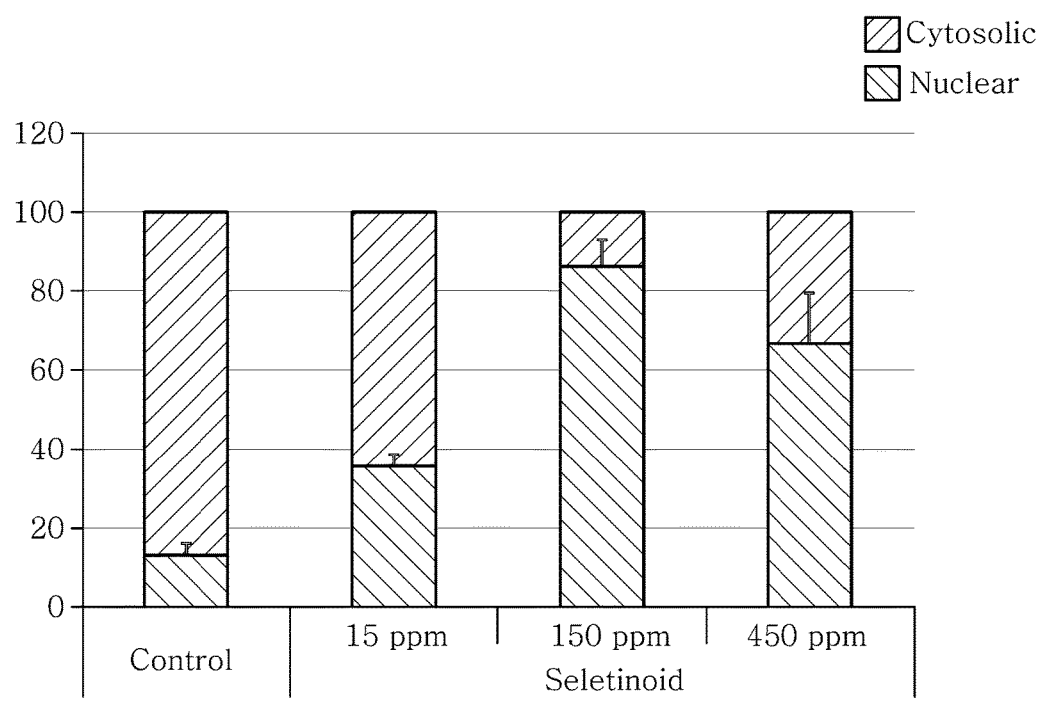

COMPOSITION FOR ACTIVATING LONGEVITY GENES, CONTAINING KOJIC ACID DERIVATIVE AS ACTIVE INGREDIENT

CROSS-REFERENCE TO RELATED APPLICATION

This application is a U.S. National Stage Application under 35 U.S.C. § 371 of International Patent Application No. PCT/KR2016/003116 filed Mar. 28, 2016, which claims the benefit of Korean Patent Application No. 10-2015-0045129 filed on Mar. 31, 2015 and Korean Patent Application No. 10-2015-0045227 filed on Mar. 31, 2015, and all the benefits accruing therefrom under 35 U.S.C. § 119, the contents of which are herein incorporated by reference in their entireties. The International Application was published in Korean on Oct. 6, 2016 as WO 2016/159604.

TECHNICAL FIELD

The present disclosure relates to a composition for activating longevity genes, specifically the Sirt-1, Klotho, XPD, ERCC8 and FoxO3a genes, which comprises a kojic acid derivative as an active ingredient.

BACKGROUND ART

Retinoids refer to retinol, retinoic acid or derivatives thereof. The retinoids exhibit various biological functions. In connection with skin, effects on hyperkeratinization and acne have been reported and the efficacy of retinoids such as retinol, retinoic acid, etc. for anti-aging is well known (Dermatologic clinics, 1998, 16, 357-364). Despite the positive effects of retinoids, they are restricted in use because even a small amount can cause skin irritation and they are unstable and easily oxidized and denatured when exposed to the air. Although studies have been conducted to stabilize retinoids, the skin irritation problem or safety problem has not been solved yet.

Researches on aging have been focused mainly on photoaging and intrinsic aging. For photoaging, methods for blocking UV and preventing change caused by UV radiation have been actively studied. Also, methods for alleviating age-related intrinsic aging have been studied. Recently, researches are focused on methods for regulating all the aging phenomena. In particular, studies are being conducted on prevention of aging and extension of life span based on the researches about the genes regulating the aging and life span of individuals.

The above information disclosed in the Background section is only for enhancement of understanding of the background of the invention and it may therefore contain information that does not form the prior art that is already known to a person of ordinary skill in the art.

DISCLOSURE

Technical Problem

In an aspect, the present disclosure is directed to providing a composition which activates the Sirt-1, Klotho, XPD, ERCC8 or FoxO3a gene, which are longevity genes related with inhibiting a cancer or extension of life span.

In another aspect, the present disclosure is directed to providing a composition which is effective in extending the life span of skin cells, moisturizing skin or strengthening the skin barrier by activating the Sirt-1, Klotho, XPD, ERCC8 or FoxO3a gene, which are longevity genes, using a kojic acid derivative capable of specifically binding to the retinoic acid receptor (RAR) so as to resolve the skin irritation problem and formulation instability of retinoids as a formulation for external application to skin.

Technical Solution

In an aspect, the present disclosure provides a composition for activating one or more gene selected from a group consisting of Sirt-1, Klotho, XPD, ERCC8 and FoxO3a, which comprises a kojic acid derivative represented by Chemical Formula 1, a salt thereof, a prodrug thereof, a hydrate thereof, a solvate thereof or an isomer thereof as an active ingredient:

[Chemical Formula 1]

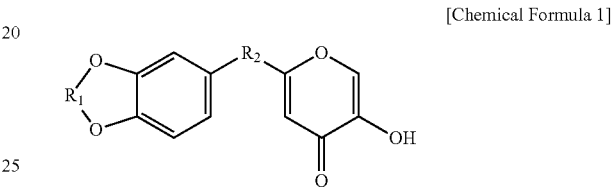

wherein $R_1$ is —$CH_2$— or —$CH_2CH_2$—, and $R_2$ is —C(O)OCH$_2$—, —CH=CHC(O)OCH$_2$— or —CH=CH—.

In an exemplary embodiment, the kojic acid derivative may be kojyl methylenedioxycinnamate represented by Chemical Formula 2:

[Chemical Formula 2]

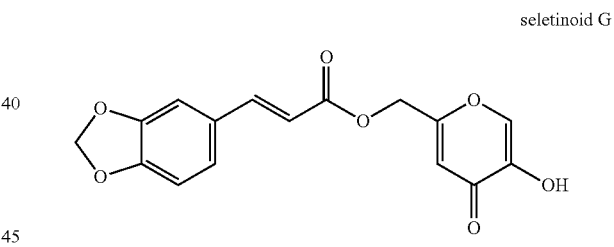

seletinoid G

In an exemplary embodiment, the kojic acid derivative, the salt thereof, the prodrug thereof, the hydrate thereof, the solvate thereof or the isomer thereof may be comprised in an amount of 0.00001-10 wt % based on the total weight of the composition.

In an exemplary embodiment, the composition may be for increasing the expression of one or more protein selected from a group consisting of Sirt-1, Klotho, XPD, ERCC8 and FoxO3a.

In an exemplary embodiment, the composition may be for inhibiting a cancer.

In an exemplary embodiment, the composition may be for inhibiting a skin cancer.

In an exemplary embodiment, the composition may be for extending life span.

In an exemplary embodiment, the composition may be for extending the life span of skin cells.

In an exemplary embodiment, the skin cell may be a dermal fibroblast.

In an exemplary embodiment, the composition may be for moisturizing skin or strengthening the skin barrier.

In an exemplary embodiment, the composition may be a composition for external application to skin.

Advantageous Effects

In an aspect, the present disclosure provides a composition which activates the Sirt-1, Klotho, XPD, ERCC8 or FoxO3a gene, which are longevity genes related with inhibiting a cancer or extension of life span.

In another aspect, the present disclosure provides a composition which is effective in extending the life span of skin cells, moisturizing skin or strengthening the skin barrier by activating the Sirt-1, Klotho, XPD, ERCC8 or FoxO3a gene, which are longevity genes, using a kojic acid derivative capable of specifically binding to the retinoic acid receptor (RAR) so as to resolve the skin irritation problem and formulation instability of retinoids as a formulation for external application to skin.

BRIEF DESCRIPTION OF DRAWINGS

FIG. 1 shows a DAPI staining result for a control group not treated with seletinoid G (Phase: transmitted, DAPI: blue, FoxO3a: red, Merge: violet). The top and bottom images show the result of two tests performed independently.

FIG. 2 shows a DAPI staining result for a test group treated with 15 ppm seletinoid G (Phase: transmitted, DAPI: blue, FoxO3a: red, Merge: violet). The top and bottom images show the result of two tests performed independently.

FIG. 3 shows a DAPI staining result for a test group treated with 150 ppm seletinoid G (Phase: transmitted, DAPI: blue, FoxO3a: red, Merge: violet). The top and bottom images show the result of two tests performed independently.

FIG. 4 shows a DAPI staining result for a test group treated with 450 ppm seletinoid G (Phase: transmitted, DAPI: blue, FoxO3a: red, Merge: violet). The top and bottom images show the result of two tests performed independently.

FIG. 5 shows a result of measuring nuclear translocation rate (control: 13.2%, 15 ppm seletinoid G: 35.7%, 150 ppm seletinoid G: 86.3%, 450 ppm seletinoid G: 66.9%). It can be seen that seletinoid remarkably activates the longevity gene FoxO3a.

BEST MODE

Hereinafter, the present disclosure is described in detail.

In an aspect, the present disclosure provides a composition for activating one or more gene selected from a group consisting of Sirt-1, Klotho, XPD, ERCC8 and FoxO3a, which comprises a kojic acid derivative represented by Chemical Formula 1, a salt thereof, a prodrug thereof, a hydrate thereof, a solvate thereof or an isomer thereof as an active ingredient:

[Chemical Formula 1]

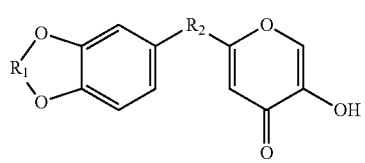

wherein $R_1$ is —$CH_2$— or —$CH_2CH_2$—, and $R_2$ is —C(O)O$CH_2$—, —CH=CHC(O)O$CH_2$— or —CH=CH—.

In another aspect, the present disclosure provides one or more selected from a group consisting of the kojic acid derivative represented by Chemical Formula 1, a salt thereof, a prodrug thereof, a hydrate thereof, a solvate thereof and an isomer thereof for use in one or more gene selected from a group consisting of activation of genes, improvement of protein expression, inhibiting a cancer, extension of life span, delaying of biological aging, improvement of symptoms of biological aging, skin moisturization, strengthening of the skin barrier or improvement of gene-related diseases.

In another aspect, the present disclosure provides a method for activating genes, increasing protein expression, inhibiting a cancer, extending life span, delaying biological aging, improving symptoms of biological aging, moisturizing skin, strengthening the skin barrier or improving gene-related diseases, which comprises administering one or more selected from a group consisting of the kojic acid derivative represented by Chemical Formula 1, a salt thereof, a prodrug thereof, a hydrate thereof, a solvate thereof and an isomer thereof or a composition for activating genes, increasing protein expression, inhibiting a cancer, extending life span, delaying biological aging, improving symptoms of biological aging, moisturizing skin, strengthening the skin barrier or improving gene-related diseases comprising the same as an active ingredient to a subject in need thereof.

In another aspect, the present disclosure provides a use of one or more selected from a group consisting of the kojic acid derivative represented by Chemical Formula 1, a salt thereof, a prodrug thereof, a hydrate thereof, a solvate thereof and an isomer thereof for preparing a composition for activating genes, increasing protein expression, inhibiting a cancer, extending life span, delaying biological aging, improving symptoms of biological aging, moisturizing skin, strengthening the skin barrier or improving gene-related diseases.

The gene is one or more selected from a group consisting of Sirt-1, Klotho, XPD, ERCC8 and FoxO3a, the protein is one or more protein selected from a group consisting of Sirt-1, Klotho, XPD, ERCC8 and FoxO3a, the cancer comprises a skin cancer, the life span comprises the life span of skin cells, the biological aging comprises skin aging and the improvement comprises one or more of prevention, treatment or improvement.

In an exemplary embodiment, the kojic acid derivative may be kojyl methylenedioxycinnamate represented by Chemical Formula 2.

[Chemical Formula 2]

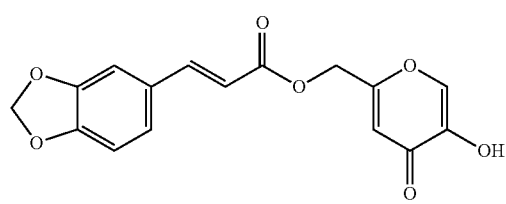

In the present disclosure, a "salt" or a "pharmaceutically acceptable salt" refers to a salt according to an aspect of the present disclosure which is pharmaceutically acceptable and has a desired pharmacological activity of its parent compound.

It comprises a common salt formed from an inorganic acid, an organic acid, an inorganic base or an organic base and an acid addition salt of a quaternary ammonium ion. The salt may comprise: (1) an acid addition salt formed from an inorganic acid such as hydrochloric acid, hydrobromic acid, sulfuric acid, nitric acid, phosphoric acid, etc. or an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tert-butylacetic acid, lauryl sulfuric acid, gluconic acid, glutamic acid, hydroxynaphthoic acid, salicylic acid, stearic acid or muconic acid; or (2) a salt formed when an acidic proton present in the parent compound is replaced. Specific examples of a basic salt comprise salts of sodium, lithium, potassium, magnesium, aluminum, calcium, zinc, N,N'-dibenzylethylenediamine, chloroprocaine, choline, diethanolamine, ethylenediamine, N-methylglucosamine and procaine.

In the present disclosure, "pharmaceutically acceptable" means approved or approvable by a regulatory agency of the government or a regulatory authority or listed in the Pharmacopoeia or other generally recognized pharmacopoeia for use in animals, more specifically in human, since significant toxic effect can be avoided when used with a common medicinal dosage.

In the present disclosure a "prodrug" refers to a drug whose physical and chemical properties have been changed such that it does not exhibit physiological activity as it is but exerts medicinal effect after it is converted to the original drug through chemical or enzymatic action in vivo. After being administered, the prodrug is metabolized and chemically converted to the active drug. In general, the prodrug is a functional derivative of the compound of the present disclosure and is easily converted to the desired compound in vivo. A method of selecting and preparing an suitable prodrug derivative is described, for example, in ["Design of Prodrugs", H Bund Saard, Elsevier, 1985]. The entire contents of this literature are incorporated hereby by reference.

In the present disclosure, a "hydrate" refers to a compound to which water is bound. The term is used in a broad concept, comprising an inclusion compound which lacks chemical bonding between water and the compound.

In the present disclosure, a "solvate" refers to a higher-order compound formed between a solute molecule or ion and a solvent molecule or ion.

In the present disclosure, an "isomer" refers to a compound with the same chemical formula but with a different chemical structure. The isomers include structural isomers, geometric isomers, optical isomers and stereoisomers. A structural isomer refers to a compound with the same molecular formula but different properties due to different structure. A geometric isomer refers to an isomer which is different in the spatial arrangement of atoms or groups of atoms combined with two atoms joined by a double bond. A stereoisomer refers to a compound with the same chemical structure but is different in the spatial arrangement of atoms or functional groups. Optical isomers (enantiomers) refer to two stereoisomers which are non-superimposable mirror images of each other. Diastereomers refer to stereoisomers having two or more asymmetric center of which molecules are not mirror images of each other.

In the present disclosure, the "isomer" comprises not only optical isomers (e.g., essentially pure enantiomers, essentially pure diastereomers or mixtures thereof) but also conformation isomers (i.e., isomers which are different only in angles of one or more chemical bond), position isomers (especially, tautomers) or geometric isomers (e.g., cis-trans isomers).

In the present disclosure, "essentially pure" means, for example, when used in connection with enantiomers or diastereomers, that the specific compound as an example of the enantiomer or the diastereomer is present in an amount of about 90% (w/w) or more, specifically about 95% or more, more specifically about 97% or more or about 98% or more, further more specifically about 99% or more, even more specifically about 99.5% or more.

In the present disclosure, "gene activation" means facilitation of a process in which a particular gene on a chromosomal DNA in transcribed and translated into a protein. That is to say, it means facilitation of gene expression, so that the function of the gene can be exerted well through facilitated transcription into a mRNA and translation into a protein.

The Sirt-1, Klotho, XPD, ERCC8 and FoxO3a genes are known as longevity genes related with life span.

Sirt-1 (silent mating type information regulation 2 homolog; sirtuin 1) is a $NAD^+$—dependent deacetylase. The human Sirt-1 gene is located on 69.64-69.68 Mb of chromosome 10 and has a mRNA sequence of NM_001142498. The protein sequence is NP_001135970. It is known as an enzyme which regulates the function of many proteins by deacetylating the lysine residue (*Ageing Res*, vol. 1 pp. 313-326, (2002)) and is also known to be effective in inhibiting the death of aged cells.

A research team at Harvard Medical School reported that calorie restriction increases life span by increasing the activity of Sirt-1 (*Science.* 2004 Jul. 16; 305(5682): 390-2. Epub 2004 Jun. 17.). It is very similar to the Sir2 of yeast which has $NAD^+$—dependent class III histone deacetylation activity. In particular, it regulates the function of transcription factors such as nuclear factor-kB, p53, etc. by cleaving the acetyl group (*Cancer Res*, vol. 64, pp. 7513-7525, (2004); *Cell*, vol. 107, pp. 149-159, (2001); *Trends Endocrinol Metab*, vol. 17, pp. 186-191, (2006)).

Sirt-1 is involved in chromatin reconstruction, DNA damage response, extension of life span associated with calorie restriction, etc., which are related with inhibition of gene expression (Chen et al., Science 310, 1641, 2005). Also, Sirt-1 is known to be involved in allergic respiratory diseases (*J Allergy Clin Immunol.* 2010 February; 125(2): 449-460. e14. doi: 10.1016/j.jaci.2009.08.009. Epub 2009 Oct. 27.). Like yeast's Sir2, Sirt-1 reconstructs chromatin and inhibits gene expression through deacetylation of histone and also induces the deacetylation of various transcription factors related with cellular growth, stress responses, endocrine regulation, etc.

Recently, a method of treating diabetes, obesity, neurodegenerative diseases, aging-associated diseases, etc. by increasing the deacetylation activity of Sirt-1 has been reported. That is to say, Sirt-1 is reported to be involved in gene expression, sugar metabolism, insulin production, inflammatory responses, protection of brain cells, etc., regulate cellular growth, aging and death and be involved in the onset of various aging-associated diseases such as cancers, metabolic diseases, obesity, inflammatory diseases, diabetes, cardiac diseases, neurodegenerative diseases, etc. at the level of tissues and organisms.

Klotho is an enzyme encoded by the KL gene. This gene encodes a type-I membrane protein that is related to β-glucuronidases. The human Klotho gene is located on 33.59-33.64 Mb of chromosome 13 and has a mRNA sequence of NM_004795. The protein sequence is NP_004786.

Klotho knockout mice show quickly increasing aging phenomena as well as arteriosclerosis related with the increased level of $1.25(OH)_2D_3$, vascular calcification, soft tissue calcification, pulmonary emphysema, decreased activity, gonadal dysgenesis, infertility, skin atrophy, ataxia, hypoglycemia and hyperphosphatemia (Mutation of the mouse Klotho gene leads to a syndrome resembling ageing. *Nature* 1997; 390, 45-51). On the contrary, overexpression of the Klotho protein leads to extended life span, increased insulin resistance, increased IGF-1 resistance, etc. (Kurosu et al., 2005).

Also in human, the single nucleotide polymorphism of the longevity gene Klotho is reported to be related to decreased life span, osteoporosis, stroke and coronary artery disease (Arking et al., 2002, Kawano et al., 2002; Mullin et al., 2005, Ogata et al., 2002; Yamada et al., 2005). In addition, it has been found out that high level of the Klotho protein leads to extended life span of brain cells, decreased occurrence of cardiac diseases and related diseases and enhanced cognitive abilities such as attention, memory, cognition, etc. and deficiency of the protein accelerates aging. However, study has not been conducted on the relationship between skin cells and Klotho expression or on the substances that can increase Klotho expression.

The XPD (ERCC2; excision repair cross-complementation group 2) protein is a member of the DNA repair machinery which maintains DNA conservation. It is one of two enzymes involved in DNA unwinding. Because it performs nucleotide excision repair, which is one of DNA repair mechanisms, together with the other XP protein, damage to the XPD gene can cause various skin diseases and aging (*Mol Cell.* 2003 June; 11(6): 1635-46.). The human XPD gene is located on 45.85-45.87 Mb of chromosome 19 and has a mRNA sequence of NM_000400. The protein sequence is NP_000391.

Defect in DNA repair causes aging-associated diseases by accelerating aging (Best, BP (2009). "Nuclear DNA damage as a direct cause of aging". *Rejuvenation Research* 12(3): 199-208.) and increases the risk of cancer (Bernstein C, Bernstein H, Payne C M, Garewal H. DNA repair/proapoptotic dual-role proteins in five major DNA repair pathways: fail-safe protection against carcinogenesis. *Mutat Res.* 2002 June; 511(2): 145-78. Review.).

Mutation of the XPD gene, which is a DNA repair protein, can cause xeroderma pigmentosum, Cockayne syndrome and trichothiodystrophy. Xeroderma pigmentosum is a recessive genic, highly photosensitive skin disease with a high risk of developing into skin cancer. It is caused by the mutation of the genes involved in DNA repair. Cockayne syndrome is a kind of dwarfism characterized by retarded growth, abnormal photosensitivity or premature aging. This disease is also known to be caused by the defect in DNA repair genes. The genes causing Cockayne syndrome are also involved in protein production and are thought to be caused by abnormal production and accumulation of proteins in cells. There are four types of Cockayne syndrome, comprising one occurring in individuals suffering from xeroderma pigmentosum. Trichothiodystrophy is a disorder characterized by brittle hair due to deficiency in sulfur-comprising protein. The protein known as the common cause of these three diseases is the DNA repair protein XPD.

ERCC8 (excision repair cross-complementation group 8) is also a protein which plays an important role in DNA repair. The human ERCC8 gene is located on 60.17-60.24 Mb of chromosome 5 and has a mRNA sequence of NM_000082. The protein sequence is NP_000073. Mutation of ERCC8 may cause Cockayne syndrome which is a genetic disorder accompanied by premature aging. This suggests that ERCC8 has a significant role in aging.

The FoxO3a gene is known as a longevity gene related with life span. FoxO3a is a protein encoded by FoxO3 (forkhead box O3) which is known as a longevity gene. It is a transcription factor involved in the insulin signaling pathway and a protein involved in the expression of enzymes such as Mn-SOD and catalase. The human FoxO3 gene is located on 108.88-109.01 Mb of chromosome 6 and has a mRNA sequence of NM_001455. The amino acid sequence is NP_001446. Activation of FoxO3a leads to antiaging effect through, for example, activation of defensive mechanisms in vivo.

The FoxO3 protein is also known as an anticancer agent (Myatt SS, Lam EW (November 2007). "The emerging roles of forkhead box (Fox) proteins in cancer". *Nat. Rev. Cancer* 7 (11): 847-59.). Activation of the FoxO3 gene is known to be related with carcinogenesis and decreased activity of the gene is often found in cancer. The FoxO3 gene is also known to be involved in inflammatory diseases caused by proliferation of lymphocytes (*Immunity* 2004. 21: 203-213., *Proc. Natl. Acad. Sci.* 2004. 101: 2975-2980., *Cell* 1999. 96: 857-868).

In an exemplary embodiment, the kojic acid derivative, the salt thereof, the prodrug thereof, the hydrate thereof, the solvate thereof or the isomer thereof may be comprised in an amount of 0.00001-10 wt % based on the total weight of the composition so as to provide superior efficacy and formulation stability without side effects. The kojic acid derivative, the salt thereof, the prodrug thereof, the hydrate thereof, the solvate thereof or the isomer thereof may be comprised in an amount of more specifically 0.0001-5 wt %, further more specifically 0.0005-3 wt %, even more specifically 0.001-2 wt %, based on the total weight of the composition.

In an exemplary embodiment, the composition may be for increasing the expression of one or more protein selected from a group consisting of Sirt-1, Klotho, XPD, ERCC8 and FoxO3a.

In an exemplary embodiment, the composition may be for inhibiting a cancer.

In an exemplary embodiment, the composition may be for inhibiting a skin cancer.

In an exemplary embodiment, the composition may be for extending life span, delaying biological aging or improving symptoms of biological aging.

In an exemplary embodiment, the composition may be for extending the life span of skin cells.

In an exemplary embodiment, the skin cell may be a dermal fibroblast.

In an exemplary embodiment, the composition may be for moisturizing skin or strengthening the skin barrier.

In an exemplary embodiment, the composition may be for preventing, improving or treating a disease related with the Sirt-1, Klotho, XPD, ERCC8 or FoxO3a gene.

A disease related with Sirt-1 refers to a disease caused by deficiency, inhibition, etc. of the Sirt-1 protein, which is an enzyme that regulates the function of many proteins by deacetylating the lysine residue. Specifically, it may be a cancer, diabetes, a neurodegenerative disease, obesity, an inflammatory disease, an allergic respiratory disease, etc.

The neurodegenerative disease may be Alzheimer's disease, amyotrophic lateral sclerosis, Parkinson's disease, Huntington's disease or multiple sclerosis and the inflammatory disease may be dermatitis, allergy, conjunctivitis, gingivitis, rhinitis, otitis media, pharyngitis, tonsillitis, pneumonia, gastric ulcer, duodenal ulcer, hepatitis, esophagitis, gastritis, enteritis, pancreatitis, colitis, nephritis, arthritis, anasarca or local edema.

A disease related with Klotho refers to a disease caused by deficiency, etc. of the Klotho protein. Specifically, it may be a cancer, arteriosclerosis, osteoporosis, stroke, Alzheimer's disease, etc.

A disease related with XPD refers to a disease caused by the DNA repair protein XPD, which affects defect in DNA repair. Specifically, it may be a cancer, xeroderma pigmentosum, Cockayne syndrome, trichothiodystrophy, etc.

A disease related with ERCC8 refers to a disease caused by the DNA repair protein ERCC8, which affects defect in DNA repair. Specifically, it may be a cancer, Cockayne syndrome, etc.

A disease related with FoxO3 refers to a disease caused by the activation or inhibition of the FoxO3 gene. Specifically, it may be a cancer, a neurodegenerative disease, an inflammatory disease, etc. Examples of the neurodegenerative disease comprise Alzheimer's disease, Parkinson's disease, Lou Gehrig's disease, Huntington's disease, multiple sclerosis, etc. Examples of the inflammatory disease comprise dermatitis, allergy, conjunctivitis, gingivitis, rhinitis, otitis media, pharyngitis, tonsillitis, pneumonia, gastric ulcer, duodenal ulcer, hepatitis, esophagitis, gastritis, enteritis, pancreatitis, colitis, nephritis, arthritis, anasarca, local edema, etc.

In an exemplary embodiment, the composition may be a composition for external application to skin. In the present disclosure, the composition for external application to skin comprises a pharmaceutical composition and a cosmetic composition.

In an aspect, the pharmaceutical composition may further comprise a suitable carrier, excipient or diluent commonly used when preparing pharmaceutical compositions. In an aspect, the carrier, excipient or diluent that may be comprised in the composition may be lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc.

The cosmetic composition may further comprise, in addition to the kojic acid derivative, the salt thereof, the prodrug thereof, the hydrate thereof, the solvate thereof or the isomer thereof as the active ingredient, ingredients commonly used in cosmetic compositions. For example, it may comprise common adjuvants such as an antioxidant, a stabilizer, a solubilizer, a vitamin, a pigment, a colorant and a fragrance and carriers.

The cosmetic composition may be prepared into any formulation common in the art. For example, it may be formulated into a solution, a suspension, an emulsion, a paste, a gel, a cream, a lotion, a powder, a soap, a surfactant-comprising cleanser, an oil, a powder foundation, an emulsion foundation, a wax foundation, a spray, etc., although not being limited thereto. More specifically, it may be prepared into a base cosmetic such as an emollient lotion, a nourishing lotion, a lotion, a body lotion, a nourishing cream, a massage cream, a moisturizing cream, a hand cream, an essence, an eye cream, a cleansing cream, a cleansing foam, a cleansing water, a pack, a gel, a patch, a spray, powder, an oil-in-water emulsion, a water-in-oil emulsion, etc., a makeup cosmetic such as a lipstick, a makeup base, a foundation, etc., a cleanser such as a shampoo, a rinse, a body cleanser, a toothpaste, a mouth wash, etc., a hair fixative such as a hair tonic, a hair gel, a mousse, etc. or a hair cosmetic such as a hair growth promoter, a hair dye, etc.

When the formulation of the cosmetic composition of the present disclosure is a paste, a cream or a gel, an animal oil, a vegetable oil, a wax, paraffin, starch, tragacanth, a cellulose derivative, polyethylene glycol, silicone, bentonite, silica, talc, zinc oxide, etc. may be used as a carrier ingredient.

When the formulation of the cosmetic composition of the present disclosure is a powder or a spray, lactose, talc, silica, aluminum hydroxide, calcium silicate or polyamide powder may be used as a carrier ingredient. Especially, when the formulation is a spray, it may further comprise a propellant such as a chlorofluorohydrocarbon, propane/butane or dimethyl ether.

When the formulation of the cosmetic composition of the present disclosure is a solution or an emulsion, a solvent, a solubilizer or an emulsifier may be used as a carrier ingredient. For example, water, ethanol, isopropanol, ethyl carbonate, ethyl acetate, benzyl alcohol, benzyl benzoate, propylene glycol, butylene glycol, 1,3-butylglycol oil, polyoxyethylene hydrogenated castor oil, glycerol, glycerin, an aliphatic ester, phenoxyethanol, triethanolamine, polyethylene glycol, beeswax, polysorbate 60, sorbitan sesquioleate, paraffin, sorbitan stearate, lipophilic glyceryl monostearate, stearic acid, glyceryl stearate/PEG 400 stearate, carboxy polymer, sitosterol, polyglyceryl-2 oleate, ceramide, cholesterol, steareth-4, dicetyl phosphate, macadamia oil, carboxyvinyl polymer, xanthan gum, fatty acid ester of sorbitan, etc. may be used.

When the formulation of the cosmetic composition of the present disclosure is a suspension, a liquid diluent such as water, ethanol, butylene glycol or propylene glycol, a suspending agent such as ethoxylated isostearyl alcohol, polyoxyethylene sorbitol ester and polyoxyethylene sorbitan ester, microcrystalline cellulose, hydroxyethyl cellulose, sodium hyaluronate, phenoxyethanol, aluminum metahydroxide, bentonite, agar, tragacanth, etc. may be used as a carrier ingredient.

When the formulation of the cosmetic composition of the present disclosure is a surfactant-comprising cleanser, an aliphatic alcohol sulfate, an aliphatic alcohol ether sulfate, sulfosuccinic acid monoester, isethionate, an imidazolinium derivative, methyl taurate, sarcosinate, a fatty acid amide ether sulfate, an alkyl amidobetaine, an aliphatic alcohol, a fatty acid glyceride, a fatty acid diethanolamide, a vegetable oil, a lanolin derivative, an ethoxylated glycerol fatty acid ester, etc. may be used as a carrier ingredient.

Hereinafter, the present disclosure will be described in detail through formulation examples. However, the following examples are for illustrative purposes only and the scope of the present disclosure is not limited by them.

[Formulation Example 1] Capsule

A capsule was prepared according to a common capsule preparation method by mixing 10 mg of kojyl methylenedioxycinnamate, 3 mg of crystalline cellulose, 14.8 mg of lactose and 0.2 mg of magnesium stearate and filling the mixture in a gelatin capsule.

[Formulation Example 2] Liquid

A liquid was prepared according to a common liquid preparation method by dissolving 20 mg of kojyl methylenedioxycinnamate, 10 g of high-fructose corn syrup and 5 g of mannitol in an adequate amount of purified water. After adding an adequate amount of lemon flavor and making the total volume 100 mL by adding purified water, the mixture was filled in a brown bottle and then sterilized.

[Formulation Example 3] Ointment

An ointment was prepared according to a common method with the following composition (wt %).

| | |
|---|---|
| Kojyl methylenedioxycinnamate | 3.0 |
| Glycerin | 8.0 |
| Butylene glycol | 4.0 |
| Liquid paraffin | 15.0 |
| β-Glucan | 7.0 |
| Carbomer | 0.1 |
| Caprylic/capric triglyceride | 3.0 |
| Squalane | 1.0 |
| Cetearyl glucoside | 1.5 |
| Sorbitan stearate | 0.4 |
| Cetearyl alcohol | 1.0 |
| Beeswax | 4.0 |
| Antiseptic, pigment and fragrance | adequate |
| Purified water | balance |

[Formulation Example 4] Nourishing Lotion

A nourishing lotion was prepared according to a common method with the following composition (wt %).

| | |
|---|---|
| Kojyl methylenedioxycinnamate | 0.1 |
| Glycerin | 3.0 |
| Butylene glycol | 3.0 |
| Propylene glycol | 3.0 |
| Carboxyvinyl polymer | 0.1 |
| Beeswax | 4.0 |
| Polysorbate 60 | 1.5 |
| Caprylic/capric triglyceride | 5.0 |
| Squalane | 5.0 |
| Sorbitan sesquioleate | 1.5 |
| Cetearyl alcohol | 1.0 |
| Tromethamine | 0.2 |
| Antiseptic and fragrance | adequate |
| Purified water | balance |

[Formulation Example 5] Nourishing Cream

A nourishing cream was prepared according to a common method with the following composition (wt %).

| | |
|---|---|
| Kojyl methylenedioxycinnamate | 0.1 |
| Glycerin | 3.5 |
| Butylene glycol | 3.0 |
| Liquid paraffin | 7.0 |
| β-Glucan | 7.0 |
| Carbomer | 0.1 |
| Caprylic/capric triglyceride | 3.0 |
| Squalane | 5.0 |
| Cetearyl glucoside | 1.5 |
| Sorbitansearate | 0.4 |
| Polysorbate 60 | 1.2 |
| Tromethamine | 0.1 |
| Antiseptic and fragrance | adequate |
| Purified water | balance |

Hereinafter, the present disclosure will be described in detail through an example. However, the following example is for illustrative purposes only and it will be apparent to those of ordinary skill in the art that the scope of the present disclosure is not limited by the example.

Test Example. Activation of Longevity Genes Sirt-1, Klotho, XPD and ERCC8 Genes

In order to investigate the effect of the kojic acid derivative according to the present disclosure on the activation of longevity genes, the effect of kojyl methylenedioxycinnamate on the activation of Sirt-1, Klotho, XPD and ERCC8 was compared with that of retinol using normal human keratinocytes (NHKs) and normal human fibroblasts (NHFs).

Specifically, after treating the keratinocytes (NHKs) and fibroblasts (NHFs) with kojyl methylenedioxycinnamate or retinol at 10 ppm and incubating them at 37° C. for 24 hours, the relative expression of Sirt-1, Klotho, XPD and ERCC8 mRNAs was compared by isolating the total RNAs from the cells. The NHFs were purchased from Lonza (Allendale, N.J., USA) and incubated at 37° C. for 24 hours using DMEM after transferring $2 \times 10^5$ cells onto a 60-mm dish. After discarding the medium, the cells were transferred to a fresh tissue culture flask. The NHEKs (normal human epidermal keratinocytes) were purchased from Lonza (Allendale, N.J., USA) and incubated using a keratinocyte growth medium (KGM-GOLD, Lonza, Allendale, N.J., USA). After detaching the cells with 0.025% trypsin and subculturing, the cells were transferred to a fresh tissue culture flask. The cells within passage 2 were used for experiments.

The total RNAs were isolated using TRIzol™ (Invitrogen, Carlsbad, Calif., USA) according to the manufacturer's instructions. RNA concentration was measured spectrophotometrically and RNA integrity was measured using Bio-Analyzer 2100 (Agilent Technologies, Santa Clara, Calif., USA). 4 µg of RNA was reverse-transcribed to cDNA using SuperScript® III reverse transcriptase (Invitrogen, Carlsbad, Calif., USA) and then stored at −70° C. Target gene expression level was measured by quantitative real-time TaqMan RT-PCR (7500Fast, Applied Biosystems, Foster City, Calif., USA). Cycle condition was 10 minutes at 95° C., 50 cycles of 15 minutes at 95° C. and 1 minute at 60° C.

TABLE 1

Experiment with keratinocytes - relative expression of Sirt-1 mRNA

| | |
|---|---|
| Control (none) | 1.0 |
| Retinol | 4.6 |
| Kojyl methylenedioxycinnamate | 5.2 |

TABLE 2

Experiment with fibroblasts - relative expression of Sirt-1 mRNA

| | |
|---|---|
| Control (none) | 1.0 |
| Retinol | 2.5 |
| Kojyl methylenedioxycinnamate | 2.4 |

TABLE 3

Experiment with keratinocytes - relative expression of Klotho mRNA

| | |
|---|---|
| Control (none) | 1.0 |
| Retinol | 8.9 |
| Kojyl methylenedioxycinnamate | 9.1 |

TABLE 4

Experiment with fibroblasts - relative expression of Klotho mRNA

| | |
|---|---|
| Control (none) | 1.0 |
| Retinol | 2.2 |
| Kojyl methylenedioxycinnamate | 2.5 |

TABLE 5

Experiment with keratinocytes - relative expression of XPD mRNA

| | |
|---|---|
| Control (none) | 1.0 |
| Retinol | 8.2 |
| Kojyl methylenedioxycinnamate | 8.5 |

TABLE 6

Experiment with fibroblasts - relative expression of XPD mRNA

| | |
|---|---|
| Control (none) | 1.0 |
| Retinol | 2.5 |
| Kojyl methylenedioxycinnamate | 3.5 |

TABLE 7

Experiment with keratinocytes - relative expression of ERCC8 mRNA

| | |
|---|---|
| Control (none) | 1.0 |
| Retinol | 1.5 |
| Kojyl methylenedioxycinnamate | 1.9 |

TABLE 8

Experiment with fibroblasts - relative expression of ERCC8 mRNA

| | |
|---|---|
| Control (none) | 1.0 |
| Retinol | 1.3 |
| Kojyl methylenedioxycinnamate | 1.4 |

From the above tables, it can be seen that the kojic acid derivative according to the present disclosure remarkably increases the expression of the Sirt-1, Klotho, XPD and ERCC8 genes which are known as longevity genes. That is to say, it can be seen that the kojic acid derivative can activate the function of the longevity genes by activating the Sirt-1, Klotho, XPD and ERCC8 genes.

The keratinocytes which are the predominant cells in the human epidermis are deeply related with the barrier function of moisturizing skin by preventing evaporation of water and protecting the skin from external harmful factors. Accordingly, the composition according to the present disclosure, which comprises the kojic acid derivative as an active ingredient, is effective in moisturizing skin and strengthening the skin barrier by activating the Sirt-1, Klotho, XPD and ERCC8 genes in the keratinocytes which exhibit the barrier function of moisturizing skin by preventing evaporation of water and protecting the skin from external harmful factors. In addition, it can be seen that the kojic acid derivative according to the present disclosure is effective in extending the life span of skin cells, specifically the fibroblasts which are the predominant cells in the dermis, by activating the longevity genes Sirt-1, Klotho, XPD and ERCC8. These effects were significantly superior when compared to retinol.

FoxO3a Gene

In order to investigate the effect of the kojic acid derivative according to the present disclosure on the activation of longevity genes, the effect of the kojyl methylenedioxycinnamate seletinoid G on the activation of the FoxO3a gene was investigated by measuring nuclear translocation rate using human MNT1 melanoma cells purchased from Lonza.

Specifically, after treating the human melanoma cells with seletinoid G at concentrations of 15, 150 and 450 ppm for 48 hours and staining for 30 minute with a DAPI solution diluted to 1/10000, the cells were observed with a confocal laser scanning microscope (Zeiss). The degree of FoxO3a activation was evaluated based on violet fluorescence resulting from the overlapping of red and blue fluorescence.

Primary antibody: anti-FoxO3a (1:200), 4° C., overnight.
Secondary antibody: Alexa Fluor 555-conjugated goat (1:5000), room temperature, 1 hour.

It was found out that the kojic acid derivative according to the present disclosure remarkably increases the expression of the FoxO3a gene which is known as a longevity gene. That is to say, it can be seen that the kojic acid derivative activates the function of the FoxO3a gene which acts as an anticancer agent and also as a longevity gene.

While the exemplary embodiments have been shown and described, it will be understood by those skilled in the art that various changes in form and details may be made thereto without departing from the spirit and scope of this disclosure as defined by the appended claims and the equivalent thereof.

The invention claimed is:

1. A method for activating one or more genes selected from a group consisting of Sirt-1, Klotho, XPD, ERCC8, and FoxO3a, comprising administering an effective amount of koiyl methylenedioxycinnamate represented by Chemical Formula 2

[Chemical Formula 2]

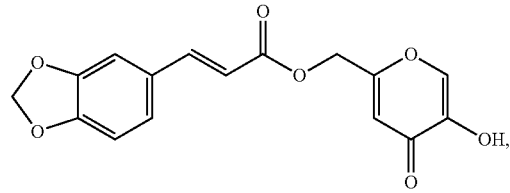

a salt thereof, a hydrate thereof, or a solvate thereof to a subject in need thereof,
Wherein the method is for extending the lifespan of skin cells, or for inhibiting a skin cancer.

2. The method according to claim 1, wherein koiyl methylenedioxycinnamate, the salt thereof, the hydrate thereof, or the solvate thereof is administered in the form of a composition comprising koiyl methylenedioxycinnamate, salt thereof, hydrate thereof, or solvate thereof in an amount of 0.00001-10 wt % based on the total weight of the composition.

3. The method according to claim 1, wherein the method is for increasing the expression of one or more proteins selected from a group consisting of Sirt-1, Klotho, XPD, ERCC8, and FoxO3a.

4. The method according to claim 1, wherein the skin cell is a dermal fibroblast.

5. The method according to claim 1, wherein the method is for moisturizing skin or strengthening skin barrier.

6. The method according to claim 2, wherein the composition is a composition for external application to skin.

* * * * *